(12) United States Patent
Ditizio

(10) Patent No.: US 7,955,870 B2
(45) Date of Patent: Jun. 7, 2011

(54) DRY ETCH STOP PROCESS FOR ELIMINATING ELECTRICAL SHORTING IN MRAM DEVICE STRUCTURES

(75) Inventor: Robert A. Ditizio, Petaluma, CA (US)

(73) Assignee: OEM Group Inc., Gilbert, AZ (US)

( * ) Notice: Subject to any disclaimer, the term of this patent is extended or adjusted under 35 U.S.C. 154(b) by 0 days.

(21) Appl. No.: 12/552,664

(22) Filed: Sep. 2, 2009

(65) Prior Publication Data

US 2010/0022030 A1    Jan. 28, 2010

Related U.S. Application Data

(63) Continuation of application No. 11/724,556, filed on Mar. 14, 2007, now Pat. No. 7,645,618.

(60) Provisional application No. 60/783,175, filed on Mar. 16, 2006.

(51) Int. Cl.
*H01L 21/00*    (2006.01)

(52) U.S. Cl. ............ 438/3; 438/48; 438/59; 257/71; 257/298

(58) Field of Classification Search ............. 438/3, 48, 438/59, 396; 257/71, 298, 303, 414, E21.208
See application file for complete search history.

(56) References Cited

U.S. PATENT DOCUMENTS

| | | | | |
|---|---|---|---|---|
| 5,854,116 | A * | 12/1998 | Ohmi et al. | 438/330 |
| 6,815,248 | B2 * | 11/2004 | Leuschner et al. | 438/59 |
| 2002/0038681 | A1 * | 4/2002 | Nakatani et al. | 148/421 |

* cited by examiner

*Primary Examiner* — Phuc T Dang
(74) *Attorney, Agent, or Firm* — Christine Meis McAuliffe; Polsinelli Shughart PC

(57) ABSTRACT

The present invention relates generally to semiconductor fabrication and particularly to fabricating magnetic tunnel junction devices. In particular, this invention relates to a method for using the dielectric layer in tunnel junctions as an etch stop layer to eliminate electrical shorting that can result from the patterning process.

37 Claims, 16 Drawing Sheets

DRY ETCH STOP PROCESS FOR ELIMINATING ELECTRICAL SHORTING IN MRAM DEVICE STRUCTURES

CLAIM TO PRIORITY

This application claims priority to all of the following applications including U.S patent application Ser. No. 11/724,556, filed Mar. 14, 2007, now U.S. Pat. No. 7,645,618, entitled "DRY ETCH STOP PROCESS FOR ELIMINATING ELECTRICAL SHORTING IN MRAM DEVICE STRUCTURES"; and U.S. Provisional Application No. 60/783,157, filed Mar. 16, 2006 entitled "DRY ETCH STOP PROCESS FOR ELIMNATING ELECTRICAL SHORTING IN MRAM DEVICE STRUCTURES".

FIELD OF THE INVENTION

The present invention relates generally to semiconductor fabrication and particularly to fabricating device structures containing metal-insulator-metal layered thin film stacks such as those used in magnetic tunnel junction devices and memory devices.

BACKGROUND OF THE INVENTION

Layered films of metal-insulator-metal are employed as storage elements in memory devices such as magnetic random access memories (MRAM) and the like. The memory element for the MRAM technology is a patterned structure of multilayer material and is usually composed of a stack of different materials such as NiFe, CoFe, PtMn, Ru, etc., and may include insulator-like materials such as $Al_2O_3$ or MgO. A typical stack may contain as many as ten or more layers of these materials some of which are non-magnetic, some of which are magnetic, and one or two of which are insulating. The insulating films in this description are defined as oxidized or nitridized metal layers that exhibit high electrical resistance in their bulk form. To fabricate a storage element, it is necessary to deposit the materials in overlying blanket films, layer by layer, to form a patterned layer of photoresist, and to etch the films into appropriate structures.

Ion beam milling or ion bean etching processes have been employed to remove magnetoresistive materials. Ion beam milling, however, is a physical milling process. Areas that are not protected by the mask are removed by bombardment with ions. The bombardment of ions sputters or peels away the unprotected material. Ion beam milling operates with low selectivity, and the portions of the stack that are near to the edges of the mask or the boundaries of an MRAM cell body can be easily damaged.

Chemical etching techniques have also been employed to selectively remove portions of deposited layers. Examples of etching techniques include dry etching techniques and wet etching techniques.

One of the drawbacks of current etching techniques is that the profiles of MRAM structures are susceptible to electrical shorting across the thin tunnel junction. The vertical separation between the upper magnet layer above the insulating dielectric tunneling layer and the lower magnet layer below this tunneling layer is inadequate to prevent electrical shorting.

SUMMARY OF THE INVENTION

Embodiments of the present invention are directed to, among other things, fabrication of magnetic tunnel junction (MTJ) devices whereby the tunnel barrier layer serves as the stop layer during plasma overetching of the upper magnetic layer. The resulting MTJ devices exhibit superior electrical isolation across the tunnel barrier layer.

In another embodiment, the gases employed during plasma overetching preferably excludes halogen containing species which result in highly selective etching of the upper magnetic layer vis-à-vis the tunnel barrier layer. The introduction of oxygen in the gas enhances the reproducibility of the process.

In yet another embodiment, a fluorine-chlorine gas mixture is employed to partially etch the magnet layer over the tunnel barrier layer.

Finally, another embodiment is directed to corrosion plasma treatment with He and $H_2$ gas prior to or during the stripping of the photoresist mask. Optionally, rinsing with water and He and $H_2$ dehydration baking can be employed following the stripping step.

DESCRIPTION OF THE INVENTION

The present invention is based, in part, on the development of a patterning method for fabricating magnetic tunnel junction (MTJ) devices that are employed in magnetic random access memory (MRAM) devices. As further described herein, a critical aspect of the invention is that MTJ devices prepared by the inventive process afford superior electrical isolation between the magnet layers in contact with the dielectric tunnel layer in comparison to the current art.

Figure 1:
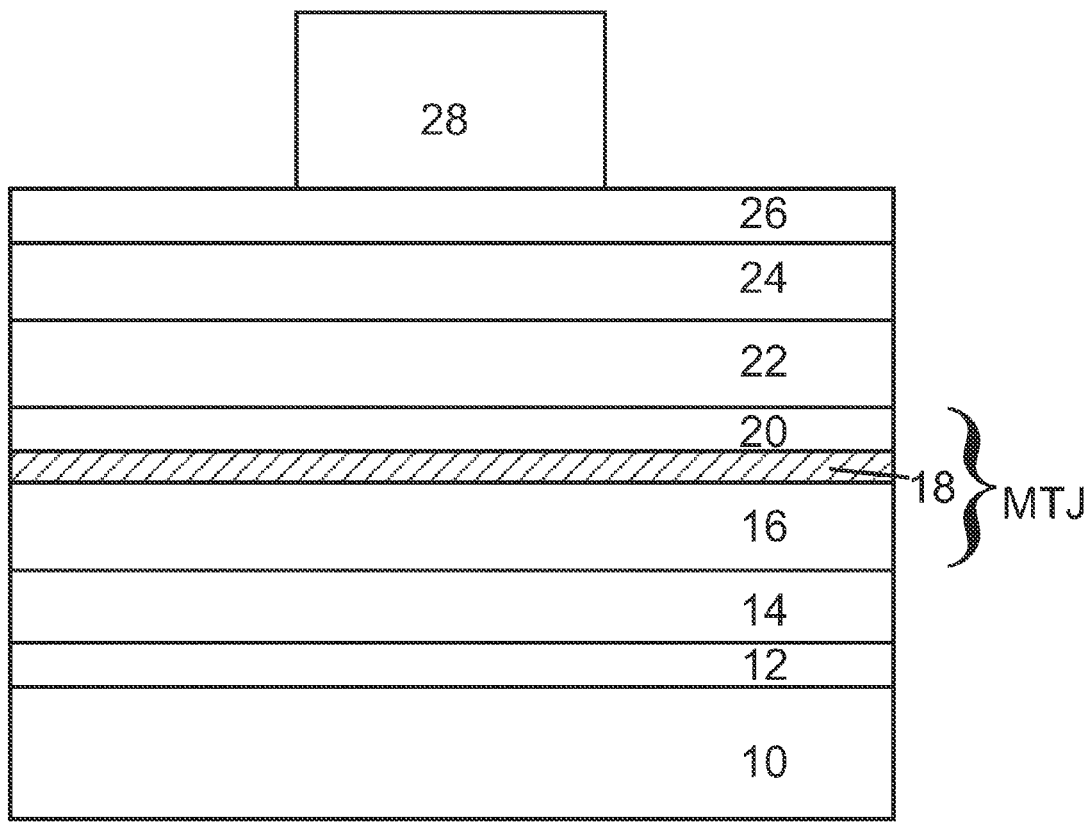
FIG. 1. Typical MRAM structure with magnetic tunneling junction.

A typical MRAM structure, within which an MTJ is contained, is shown in FIG. 1. The MRAM structure is a complex stack of magnetic, conductive, and insulating films on a substrate. In FIG. 1, the specific components of a typical MRAM structure are shown and consist of a substrate 10, a barrier layer 12, a bottom contact layer 14, a multilayer fixed magnet structure 16 consisting of layers of CoFe, Ru, NiFe, IrMn, PtMn, and the like, a dielectric tunnel layer such as alumina or MgO 18, a switchable magnet layer 20 (NiFe, CoFe, CoNiFe, CoFeB, and the like), and a top contact layer 22 (Ta, TaN, Ti, TiN, W, and the like).

Also shown in FIG. 1 is a hard mask layer 24, an antireflective coating 26, and a patterned layer of photoresist 28. photoresist layer 28 is a light sensitive material that is commonly used by those skilled in the art of electrical device fabrication as a mask to etch one or more of the underlying layers below the photoresist so that portions of the underlying layer not protected by the resist layer can be etched away. Antireflection coating 26, which is typically 300 Å to 800 Å thick, is commonly used to absorb radiation to form an optically opaque film to enhance the contrast of the imaging resist. ARC coatings effectively reduce reflections of the incident radiation back into the overlying PR mask layer. This prevents overexposure of the photoresist material. Hard mask layer 24 is commonly used in device fabrication as an intermediate mask transfer layer. When utilized, the photoresist is used as a dry etch mask to transfer the pattern into the hard mask, and possibly one or more of the underlayers, after which the hard mask layer is used as a mask to transfer the pattern into the remaining underlayers that are not defined using the photoresist. Hard masks such as silicon dioxide and silicon nitride are commonly used as a means to improve the durability of the mask relative to that of photoresist or to allow processing at temperatures above the softening point of polymeric photoresist layers.

Magnetic stack structure are typically formed on a substrate 10. The substrate 10 may include any structure that has an exposed surface. Structures are preferably those used in the manufacture of semiconductor devices such as silicon wafer, silicon-on insulator (SOI), silicon-on sapphire (SOS), aluminum titanium carbide (AlTiC) doped and undoped semiconductors, III-V or II-VI semiconductors, epitaxial layers of silicon supported by a base semiconductor foundation, and other semiconductor structures. The semiconductor need not be silicon-based. The semiconductor could be silicon-germanium, germanium, or gallium arsenide. The structure could also be a non-semiconductor such as glass or polymer. The substrate 10 may include buried electronic devices such as transistors, diodes, capacitors, and resistors, or any other device or circuit element that would be used in conjunction with the magnetic multilayer stack.

For the typical multilayer MRAM structure shown in FIG. 1, within which is contained an MTJ, it is understood that the specific layers, e.g., materials and their arrangements, that form the multilayer structure can vary. MTJ and MRAM structures are known in the art and are described, for example, in U.S. Pat. No. 6,673,675 to Yates et al., entitled "Methods of Fabricating an MRAM Device Using Chemical Mechanical Polishing"; U.S. Pat. No. 6,677,165 to Lu et al., entitled "Magnetoresistive Random Access Memory (MRAM) Cell Patterning"; U.S. Pat. No. 6,653,704 to Gurney, et al., entitled "Magnetic Memory with Tunnel Junction Memory Cells and Phase Transition Material for Controlling Current to the Cells"; U.S. Pat. No. 6,024,885 to Pendharkar, et al., entitled "Process for Patterning Magnetic Films"; and U.S. Pat. No. 5,650,958 to Gallagher, et al., entitled "Magnetic Tunnel Junctions with Controlled Magnetic Response"; all of which are incorporated herein by reference.

It should be understood that the orientation of the magnetic film stack can be reversed relative to the order shown in FIG. 1. That is, the orientation of the film structure can be such that the film stack can be deposited in reverse order with the top contact layer and free magnet layer are below the dielectric tunnel layer and the multi-layer fixed and antiferromagnetic layers are placed above the dielectric tunnel layer. It should also be understood that the magnetic tunnel junctions in orientations in which the free layer is deposited above the dielectric tunnel layer or below the dielectric tunnel layer and remain within the scope of the inventive method.

Figure 2:
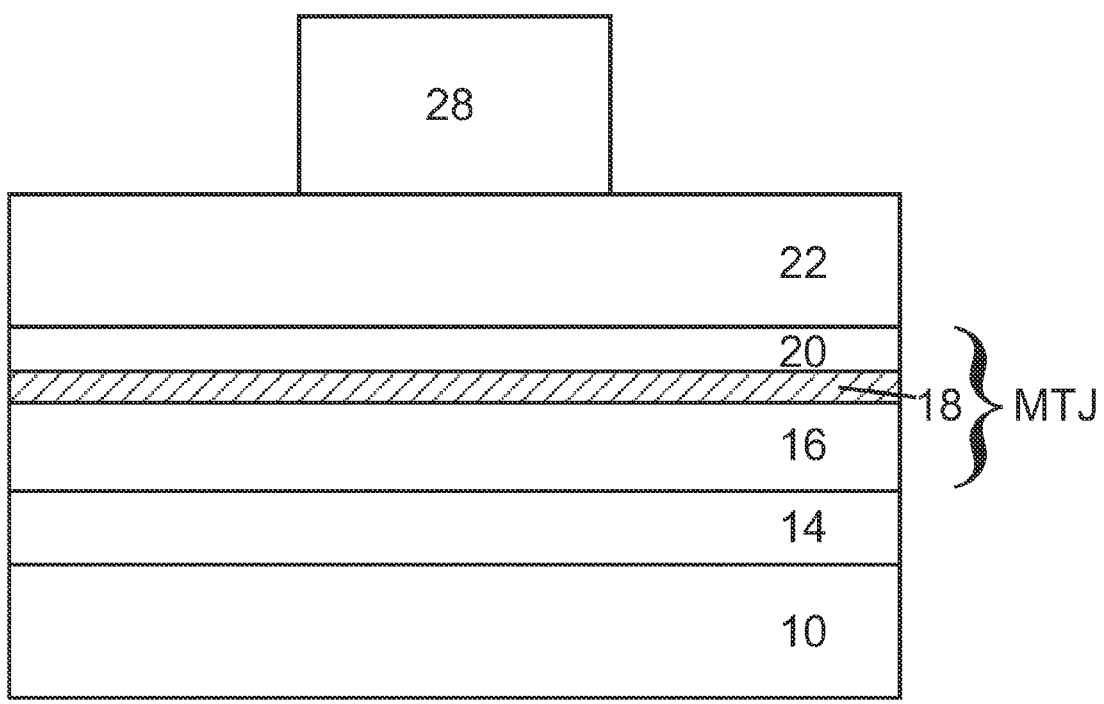
FIG. 2. Simplified MRAM structure with magnetic tunneling junction.

In one simplified embodiment shown in FIG. 2, the MTJ stack comprises a substrate 10, a bottom contact layer 14, a fixed bottom magnet layer 16, a dielectric tunnel layer 18, a switchable upper magnet layer 20, and a top contact layer 22. The stack structure is patterned with photoresist layer 28. This simplified structure is used in the following description of the preferred embodiments for the present invention.

Figure 3:
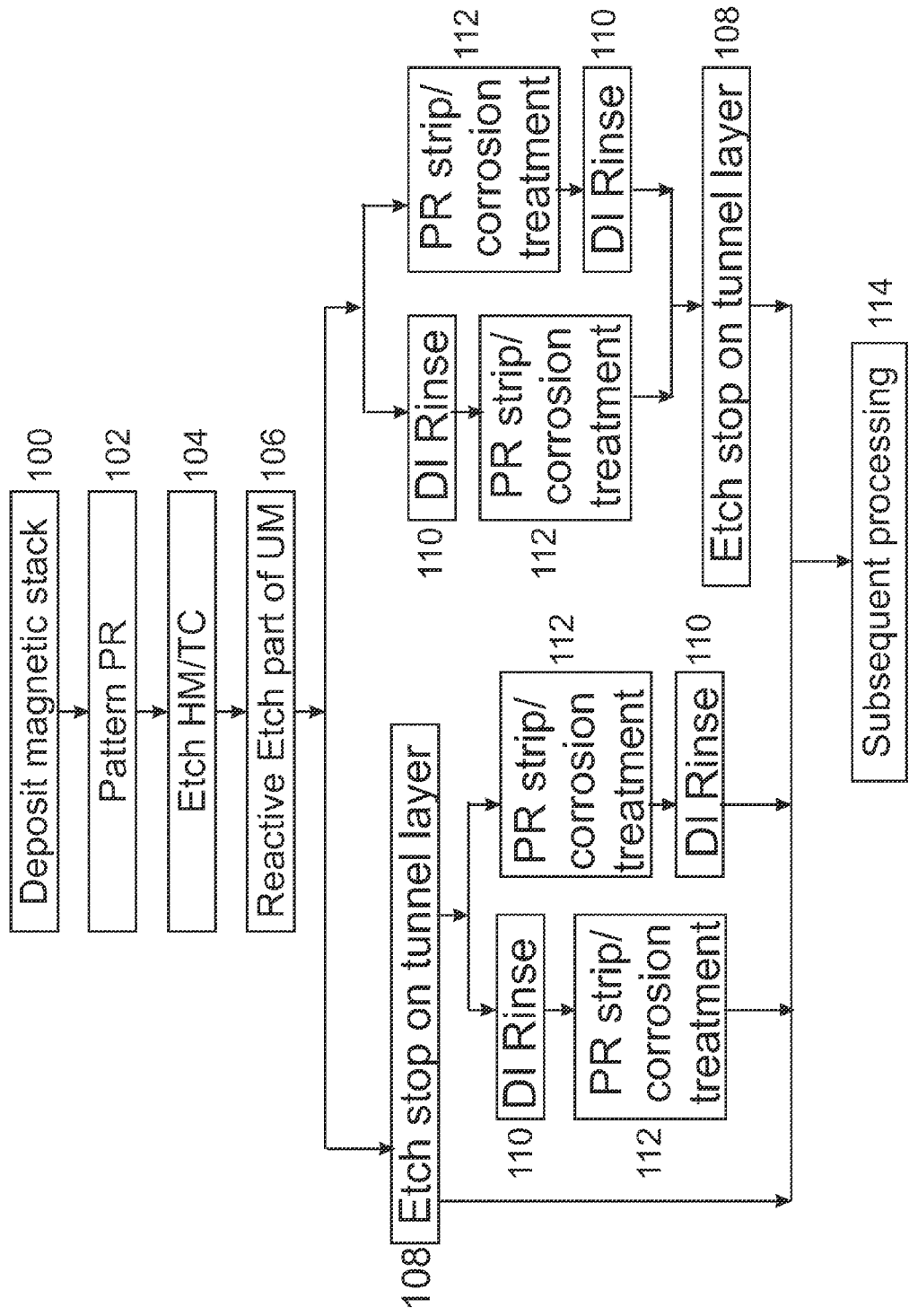
FIG. 3. Inventive MRAM process sequence.
Figure 4:
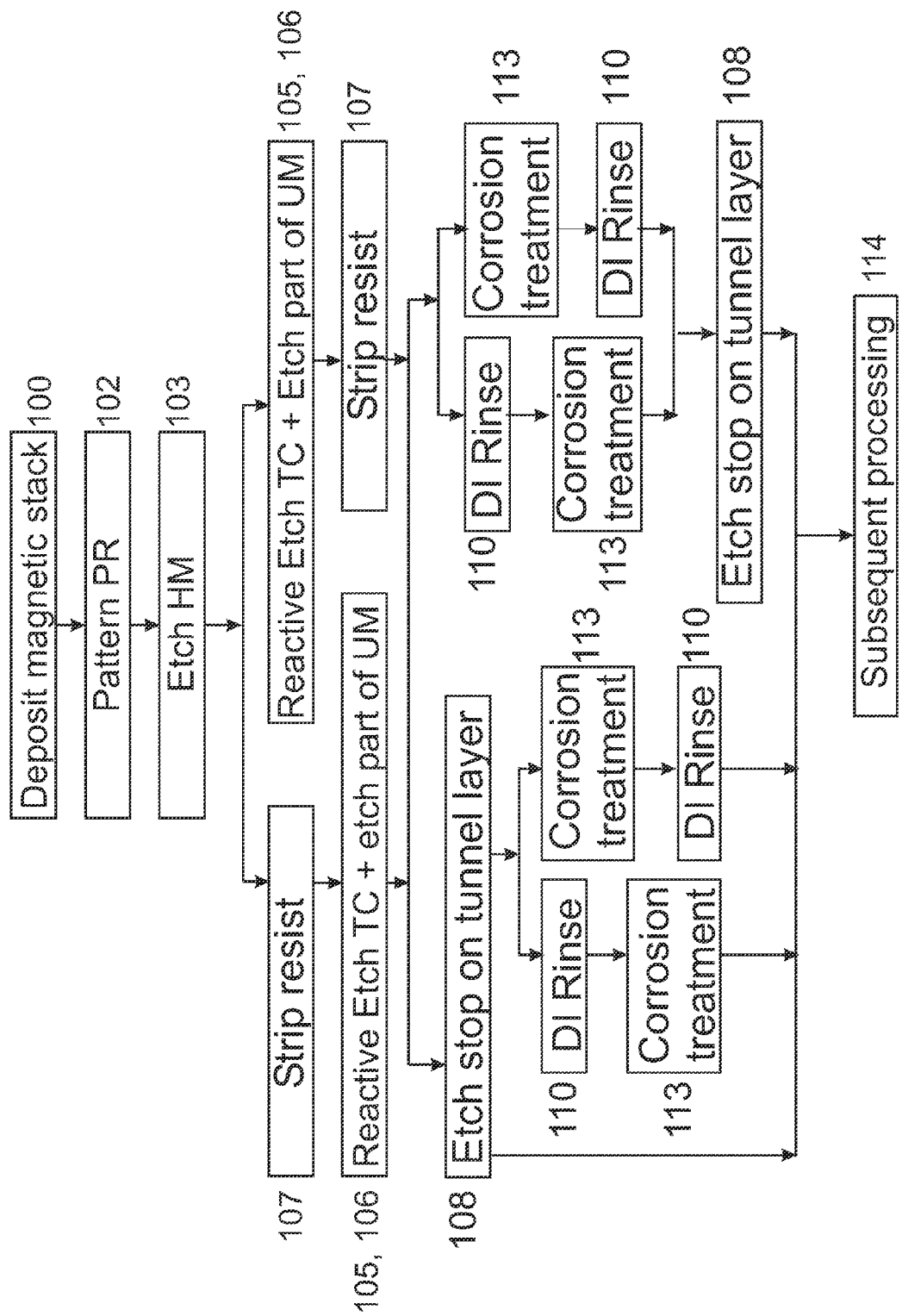
FIG. 4. Inventive MRAM process sequence.

Inventive etch-stop process sequences are provided in FIGS. 3, 4, and 5.

FIG. 3 shows an inventive process sequence in which the magnetic stack is deposited 100, the PR is patterned 102, one or both of the hard mask and top contact layers are etched 104, and a reactive etch process is used to remove part of the upper magnet layer 106. Following the reactive etch of the upper magnet layer 106, MTJ device structures are exposed to an inventive etch stop process 108 directly, or first to a corrosion treatment sequence consisting of a D1 rinse, a PR strip, and a plasma based corrosion treatment, followed by an inventive etch stop process 108.

In one embodiment shown in FIG. 3 in which the inventive etch stop process 108 directly follows the reactive partial etch of the upper magnet 106, the patterning of the MTJ device structures is completed and the devices are moved to subsequent processing 114. In a second embodiment in which the inventive etch stop process 108 directly follows the reactive partial etch of the upper magnet 106, the devices are exposed to a sequence of processes to prevent corrosion. Exposure of magnetic films to chlorine- and bromine-containing etch chemistries can product adverse reactions upon removal of the devices from vacuum and subsequent exposure of the etched films to moisture under ambient conditions. Depending on the sensitivity of the films, various sequences have been developed for preventing adverse corrosive reactions such as those shown in FIG. 3.

In one embodiment of the inventive process in which corrosion prevention treatments are employed and in which the corrosion treatments are employed following the etch stop on the tunnel layer 108, the corrosion treatment sequence consists of a D1 water rinse 110 followed by a photoresist strip/corrosion treatment 112. In a second embodiment of the inventive process in which corrosion prevention treatments are employed and in which the corrosion prevention treatments are employed following the etch stop on the tunnel layer 108, the corrosion prevention treatment sequence consists of a photoresist strip/corrosion treatment 112, followed by D1 water rinse 110.

In one embodiment shown in FIG. 3 in which the inventive etch stop process 108 does not directly follow the reactive partial etch of the upper magnet 106, but rather is preceded by corrosion prevention treatments 110 and 112. In the first embodiment shown in FIG. 3 in which the inventive etch stop process does not directly follow the reactive partial etch of the upon magnet 106, the MTJ device structures are exposed to a D1 water rinse 110 followed by a photoresist strip/corrosion treatment 112 prior to the inventive etch stop on the tunnel layer 108. In a second embodiment of the inventive process in which the inventive etch stop process 108 does not directly follow the reactive partial etch of the upper magnet 106, the devices are exposed to a photoresist strip/corrosion treatment 112 followed by a D1 water rinse prior to the inventive etch stop on the tunnel layer 108.

FIG. 4 shows an inventive process sequence in which the magnetic stack is deposited 100, the PR is patterned 102, and the hard mask is etched 103. Following the hard mask etch 103, MTJ device structures are exposed to a photoresist strip process 107 or to a reactive etch process 105 to remove the top contact layer and a reactive etch process 106 to remove part of the upper magnet. In a first embodiment of the inventive process in which the hard mask etch process 103 is followed by photoresist strip process 107, subsequent to the photoresist process 107 the MTJ devices are exposed to a reactive etch process 105 to remove the top contact layer and a reactive etch process 106 to remove part of the upper magnet. In a second embodiment of the inventive process in which the hard mask etch process 103 is followed by a reactive etch process 105 to remove the top contact layer and a reactive etch process 106 to remove part of the upper magnet, the MTJ devices are subsequently exposed to a photoresist strip process 107.

Following the combined steps of photoresist strip 107 and reactive etch processes 105 to remove the top contact layer and 106 to remove part of the upper magnet, the MTJ devices are exposed to the etch stop process 108 directly, or first to a corrosion treatment sequence consisting of a D1 rinse and a plasma based corrosion treatment 113, followed by an inventive etch stop process 108.

In one embodiment shown in FIG. 4 in which the inventive etch stop process 108 directly follows the reactive partial etch of the upper magnet 106, or follows a photoresist strip process 107 that was preceded by the reactive partial etch of the upper magnet 106, the patterning of the MTJ device structures is completed and the devices are moved to subsequent processing 114. In a second embodiment in which the inventive etch stop process 108 directly follows the reactive partial etch of the upper magnet 106, or follows a photoresist strip process 107 that was preceded by the reactive partial etch of the upper magnet 106, the devices are exposed to a sequence of processes to prevent corrosion. Exposure of magnetic films to chlorine- and bromine-containing etch chemistries can produce adverse reactions upon removal of the devices from vacuum and subsequent exposure of the etched films to moisture under ambient conditions. Depending on the sensitivity of the films, various sequences have been developed for preventing adverse corrosive reactions such as those shown in FIG. 4.

In one embodiment of the inventive process in which corrosion prevention treatments are employed following the etch stop on the tunnel layer 108, the corrosion prevention treatment sequence consists of a D1 water rinse 110 followed by a plasma-based corrosion treatment 112. In a second embodiment of the inventive process in which corrosion prevention treatments are employed and in which the corrosion prevention treatments are employed following the etch stop on the tunnel layer 180, the corrosion prevention treatment sequence consists of a plasma-based corrosion prevention treatment 112, followed by D1 water rinse 110.

In one embodiment shown in FIG. 4 in which the inventive etch stop process 108 does not directly follow the reactive partial etch of the upper magnet 106, but rather is preceded by corrosion prevention treatments 110 and 113. In the first embodiment shown in FIG. 4 in which the inventive etch stop process does not directly follow the reactive partial etch of the upper magnet 106, the MTJ device structures are exposed to a D1 water rinse 110 followed by a plasma-based corrosion treatment 113 prior to the inventive etch stop of the tunnel layer 108. In a second embodiment of the inventive process in which the inventive etch stop process 108 does not directly follow the reactive partial etch of the upper magnet 106, the devices are exposed to a plasma-based corrosion treatment 113 followed by a D1 water rinse prior to the inventive etch stop on the tunnel layer 108.

Figure 5A:
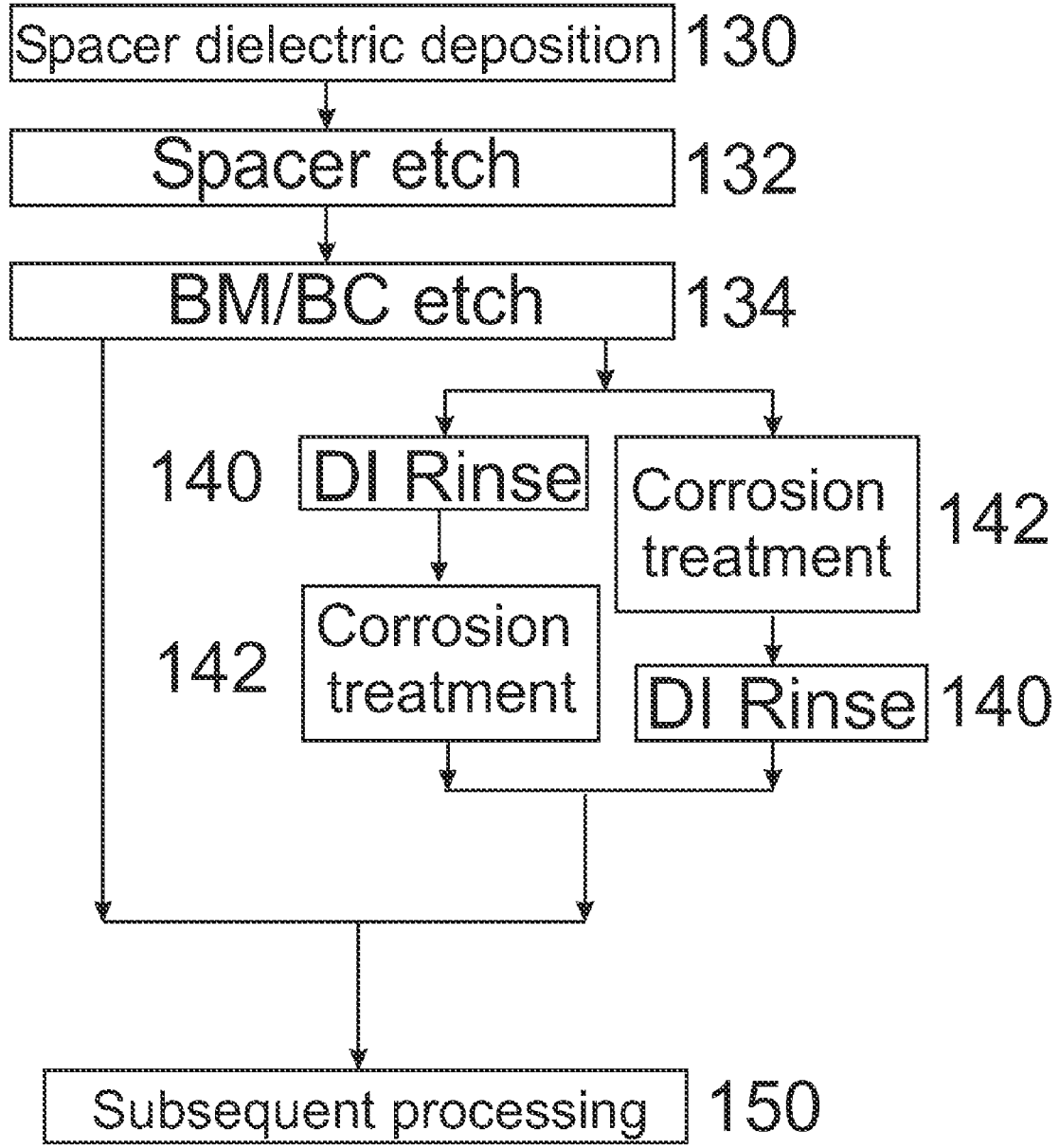
FIG. 5a. Inventive MRAM process sequence.
Figure 5B:
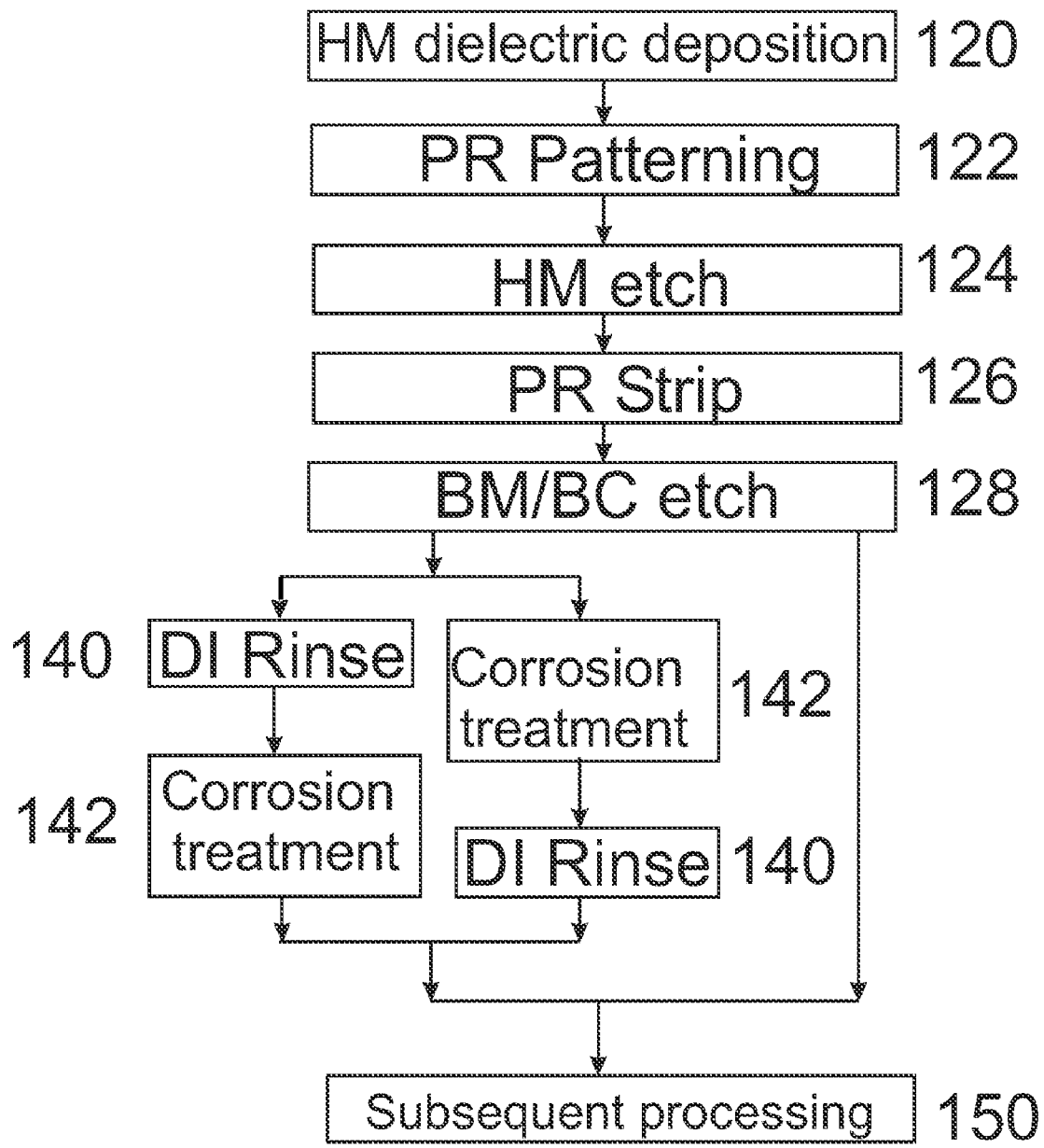
FIG. 5b. Inventive MRAM process sequence.

Two approaches to the subsequent processing 114, as indicated in FIG. 3 and FIG. 4, are shown in FIG. 5a and FIG. 5b. These figures describe two specific methods that specifically exploit the unique capability afforded by inventive etch stop process step 108.

In FIG. 5a, a spacer is used to passivate the sidewall of the MTJ device structure to prevent electrical shorting during subsequent processing. The sidewall spacer is used in conjunction with an etch stop process such as that described by etch stop process 108 shown in FIGS. 3 and 4. FIG. 5a shows the preferred embodiment for subsequent processing steps that follow the inventive etch stop process 108 shown in FIGS. 3 and 4. In this preferred embodiment, the subsequent process 114 described in FIGS. 3 and 4 consist of a spacer dielectric deposition 130, a spacer etch 132, and a bottom magnet/bottom contact etch 134 to complete the process or a bottom magnet/bottom contact etch 134 followed by a D1 water rinse step followed by a plasma-based corrosion prevention treatment 142. Alternatively, the plasma-based corrosion prevention treatment 142 can precede the D1 water rinse as shown in FIG. 5a before proceeding with subsequent processing of the device 150.

In FIG. 5b, an alternative approach to subsequent processing 114 is shown in which an insulating hard mask layer such as silicon dioxide or silicon nitride is deposited 120, photoresist is patterned 122, the hard mask is etched 124, the photoresist is stripped 126, and the bottom magnet and bottom contact are etched 128. In this approach, the photoresist patterning is such that the silicon dioxide or silicon nitride hard mask layer extends laterally beyond the vertical sidewall produced from the original hard mask etch 103, upper contact etch 105, reactive upper magnet etch 106, and etch stop process 108. The lateral extension of hard mask 120 beyond the vertical sidewall, upon photoresist patterning 122, should be such that the sidewall of the original hardmask, the upper contact, and the upper magnet layer remains covered with hard mask layer 120 after hard mask layer etch 124.

The layers that comprise the MRAM stack or other magnetic device structure are deposited 100 using techniques employed by those skilled in the art of film deposition. The films may be deposited by physical vapor deposition, chemical vapor deposition, atomic layer deposition, nano-layer deposition, atomic layer deposition, evaporation, and other techniques. The films in the stack may also be deposited by one of these methods in one form and subsequently modified in a second chamber. The alumina ($Al_2O_3$) dielectric, for example, might be formed by depositing a layer of aluminum and subsequently expositing the aluminum to an oxidizing process to form alumina. Similarly, MgO might be formed by depositing a layer of magnesium and subsequently expositing the Mg to an oxidizing process to form MgO.

A photoresist deposition and patterning step 102 is used to create a pattern for defining the MTJ or MRAM stack. Although not shown in the simplified MRAM stack example in FIG. 2, an antireflective coating can be used in conjunction with the photoresist to improve the accuracy of the pattern transfer. Additionally, a hard mask layer can be incorporated between the photoresist and the top contact layer. Hard mask layers such as silicon dioxide and silicon nitride could be used. Alternatively, the thickness of the conductive top contact layer can be made such that it can serve the dual purpose of hard mask and top contact layer. FIG. 2 shows the simplified MRAM stack structure after magnetic stack deposition 100 and subsequent photoresist patterning 102.

Figure 6:
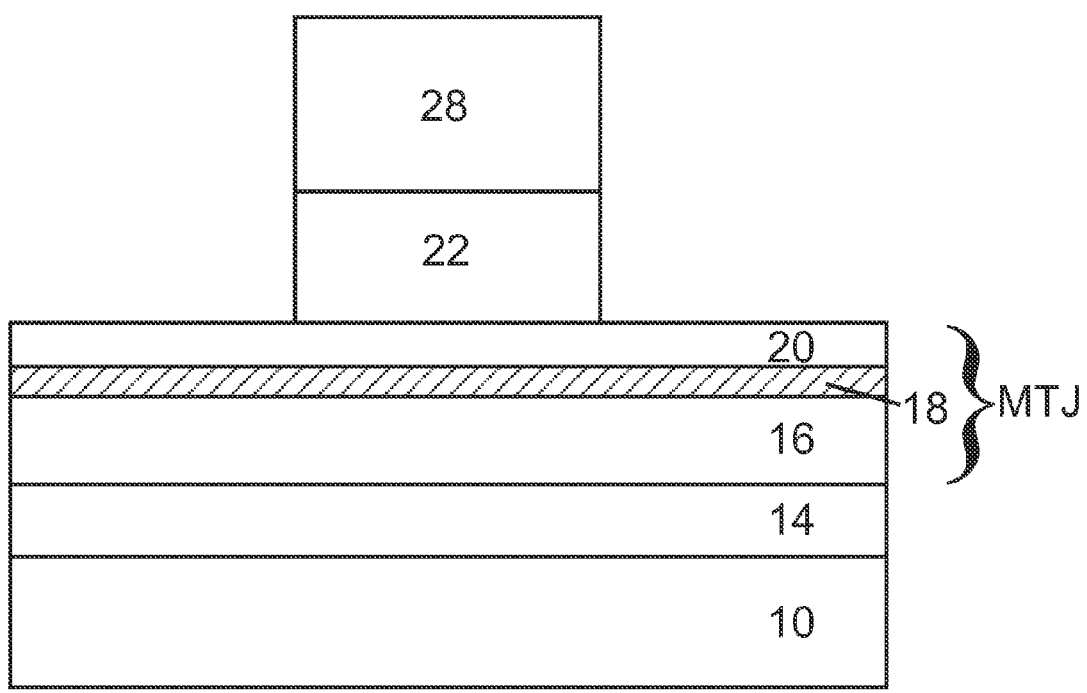
FIG. 6. MRAM stack structure after top contact patterning.

In the preferred embodiment, the hard mask layer and the upper contact layers are patterned 103 using common techniques employed by those skilled in the art. One example of a common process for reactively etching a silicon oxide hard mask, if present, is to use a mixture of $CF_4$, $CHF_3$, and Ar. Oxide etch processes are widely available in the literature. Similarly, an example of a process chemistry that is commonly used to reactively etch the top conductor layer 104, 105 is the use a mixture of $Ar/Cl_2$. Again, metal contact layer etches have been published extensively in the literature. Oxide and nitride hard masks and metal contact layers have been in use for many years and the techniques that have been used to remove these layers are apparent to those skilled in the art. The simplified MRAM stack structure after contact etch is shown in FIG. 6.

Figure 7:
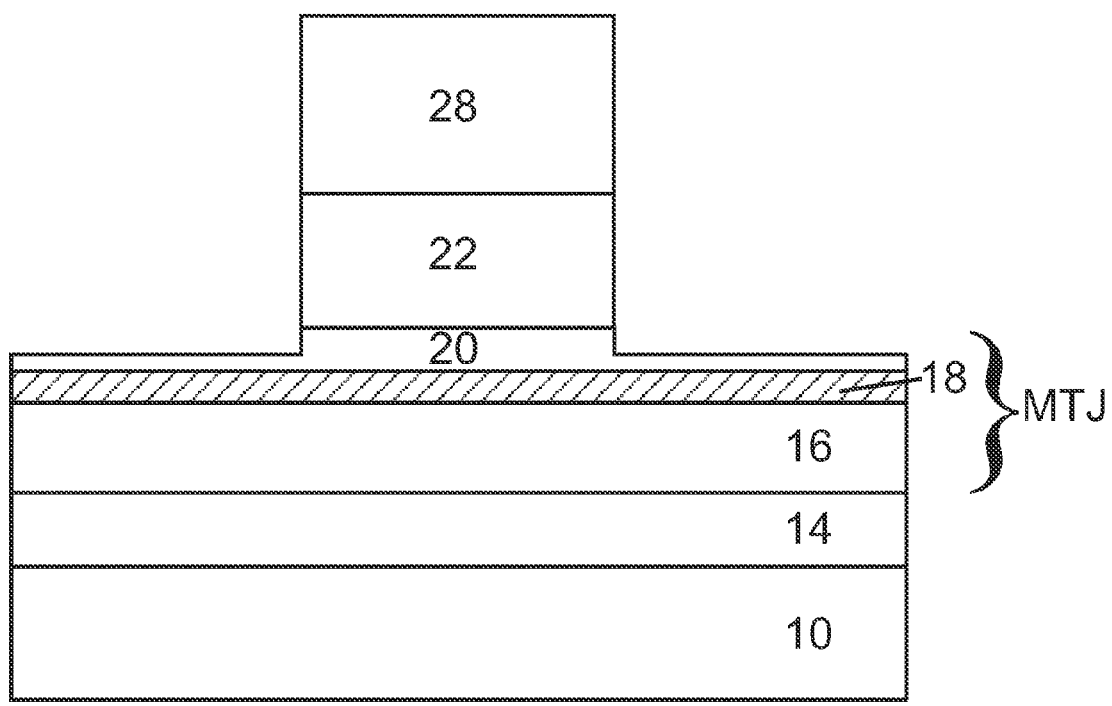
FIG. 7. MRAM stack structure after reactive magnet-layer etch step.

The removal of the magnetic layers found in a magnetic multi-layer stacks is not well established in the art. Within the scope of this invention, is the use of a process that is particularly well-suited for reactive upper magnet layer etch 106 in combination with etch stop process 108. This inventive process 106 consists of gas mixture of a chlorine-containing gas such as $Cl_2$, $SF_6$, and $CHF_3$ to remove part of the top magnet layer. Alternatively, a gas molecule that contains Cl and F atoms might be used. The ratio of chlorine-containing to fluorine-containing gases should be in the range of 2:1 to 20:1. Typical process conditions for the reactive etch step 106, demonstrated in the Spectra® inductively coupled process module manufactured by Tegal Corporation, are as follows: 400 W of 13.56 MHz rf power on the inductive source coil, 20 W of 450 kHz rf power applied to the substrate, 40 sccm $Cl_2$, 8 sccm $CF_4$, and 4 mT process pressure. The simplified MRAM stack structure after reactive magnet layer etch 106 is shown in FIG. 7.

Figure 8:
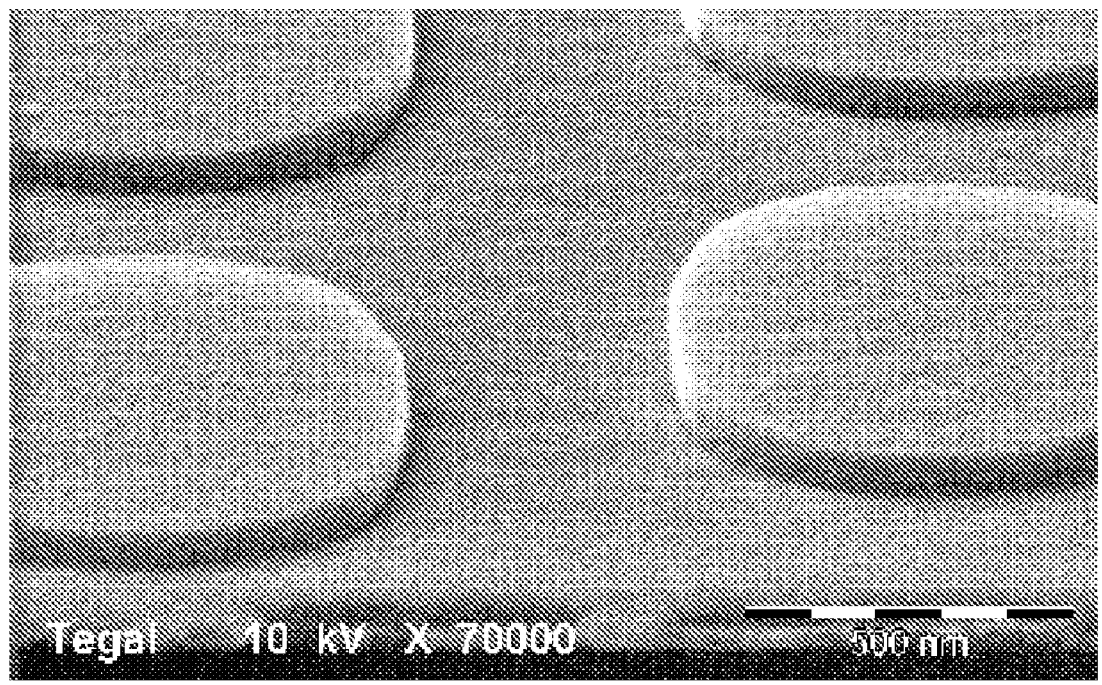
FIG. 8. MRAM stack structure after reactive magnet-layer etch.

The inclusion of fluorine as an additive to a chlorine-containing etch process has been found to produce smooth etched surfaces (as shown in FIG. 8) and prevent diffusion of the chlorine species through very thin films of magnetic material that remain after reactive upper magnet etch step 106. Use of a fluorine/chlorine containing gas mixture allows for removal of the upper magnet layer to within 5-25 Å of the interface between the remaining upper magnet layer and the underlying dielectric tunnel layer.

In the preferred embodiment of the inventive reactive upper magnet etch process 106, the remaining upper magnet layer will be etched as close as possible to the interface between the remaining upper magnet layer 20 and the underlying dielectric layer 18 without penetrating the tunneling dielectric layer in the vicinity of the features prior to moving to a subsequent processing step such as the etch stop process 108, the D1 water rinse 110, or the PR strip/corrosion treatment 112. In a preferred embodiment, the upper magnet layer 20 is etched uniformly and the underlying dielectric layer 18 is not breached anywhere on the wafer during the reactive upper magnet layer etch 106 as shown in FIG. 7.

Figure 9:
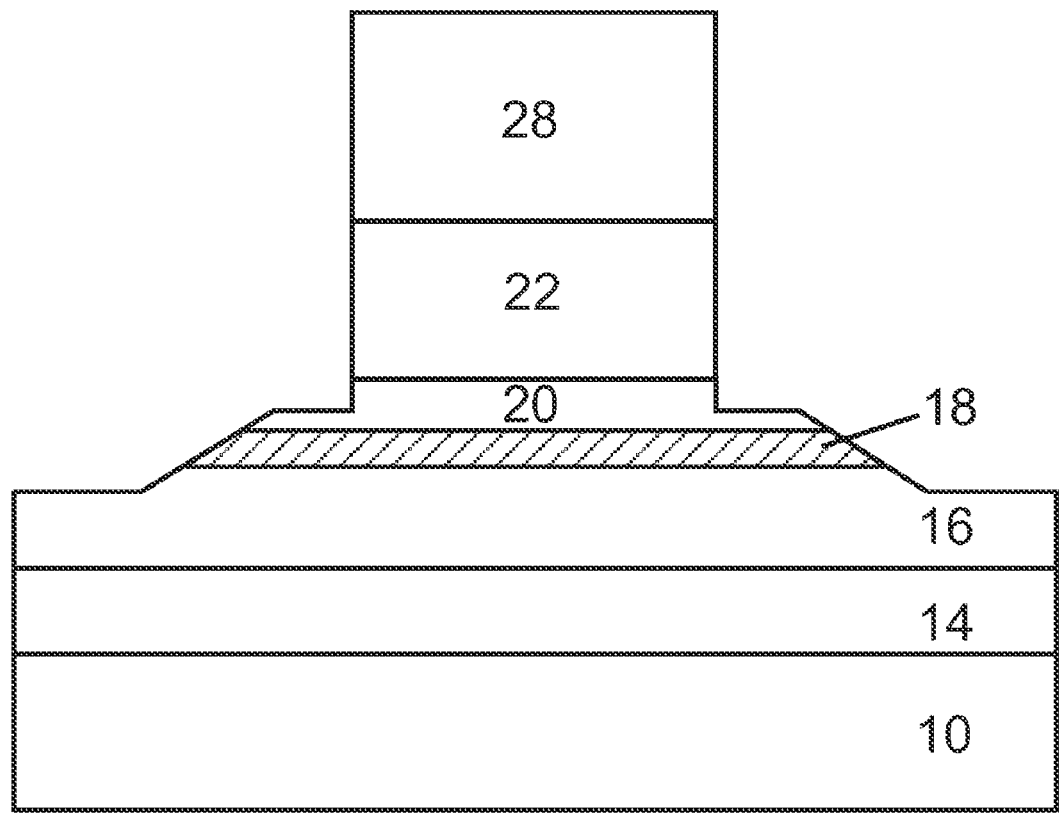
FIG. 9. Embodiment of the inventive MRAM patterning sequence in which tunneling dielectric layer is not breached in the vicinity of the feature but is breached in areas not in close proximity to the mask feature.

In one embodiment of the inventive process, however, the upper magnet layer 20 is completely removed and the underlying dielectric layer 18 is breached, but not within close proximity of the patterned MTJ stack features (See FIG. 9). In this embodiment of the inventive process, the upper magnet layer etch 106 is removed with an etch process that contains one or more of the following gases or gas mixtures: $Cl_2$, $Cl_2/Ar$, $Cl_2/CF_4$, $Cl_2/CHF_3$, $Cl_2/Ar$, $BCl_3/Cl_2$, $BCl_3/Cl_2/Ar$, $BCl_3/HBr$, $BCl_3/HBr/Ar$, $NH_3$, $NH_3/CO$.

In yet another embodiment, the upper magnet layer 20 is completely removed, the underlying dielectric layer 18 is also removed outside of a sloped region in close proximity of the patterned MTJ stack, and all or part of the bottom magnet layer 16 and all or part of the bottom contact layer 14 are removed. (See FIG. 10.) A unique benefit of this embodiment is that the full MRAM structure is patterned with a single mask; subsequent processing steps 114 are not required. In this embodiment of the inventive process, the upper magnet layer etch 106 is removed with an etch process that contains one or more of the following reactive gases and gas mixtures: $Cl_2$, $Cl_2/Ar$, $Cl_2/CF_4$, $Cl_2/CHF_3$, $Cl_2/Ar$, $BCl_3/Cl_2$, $BCl_3/Cl_2/Ar$, $BCl_{34}HBr$, $BCl_3/HBr/Ar$, $NH_3$, $NH_3/CO$.

Figure 11:
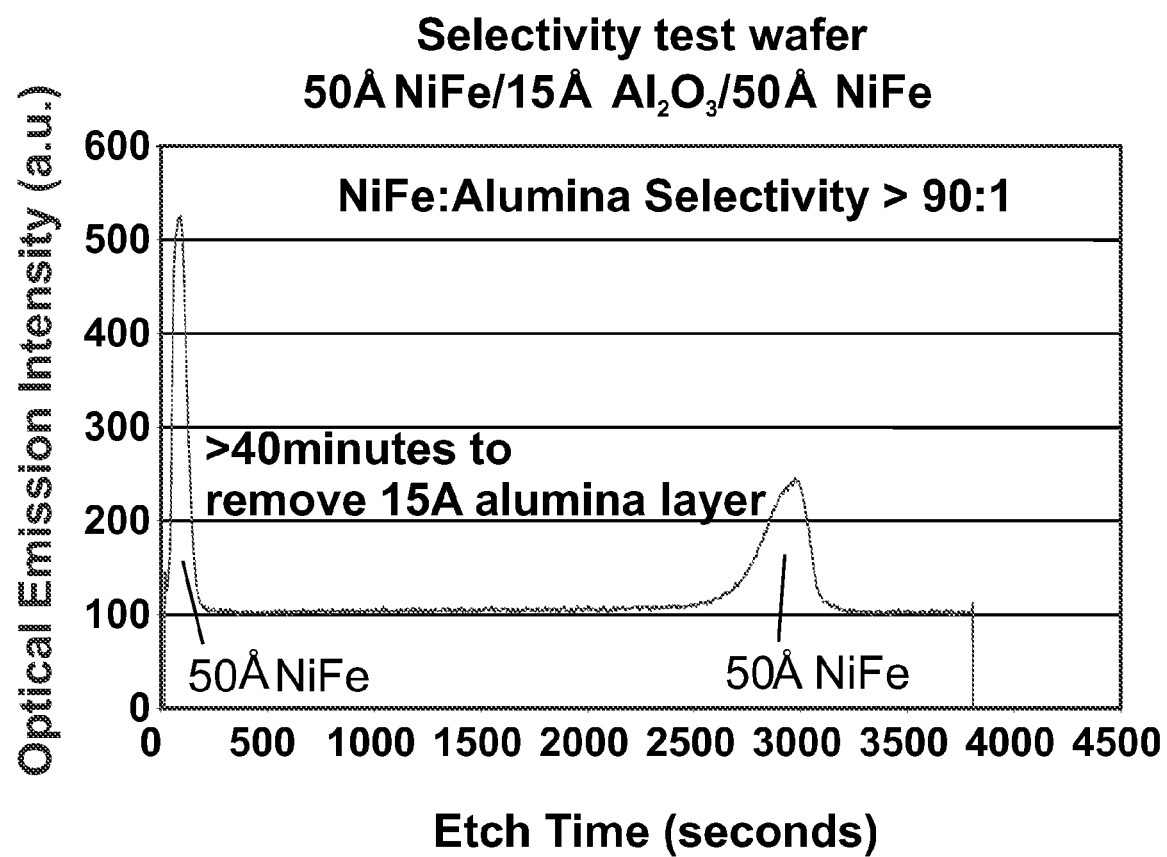
FIG. 11. Plot of optical emission signal intensity obtained during the etch of a 50 Å NiFe/15 Å alumina/50 Å NiFe stack structure. The two peaks in the plot indicate the removal of the two NiFe layers. The time between the two peaks indicate the time required to remove the 15 Å alumina layer. The NiFe-to-alumina etch selectivity obtained from the process used to produce the graph is greater than 90:1.

The remainder of the upper magnet layer that is not removed in the reactive step 106, in the aforementioned embodiments is subsequently removed using etch stop process 108 consisting, in the preferred embodiment, of a mixture of a non-reactive gas such as argon and an oxidizing gas, such as oxygen, whereby the dielectric of the tunnel barrier layer serves as the stop layer. In the preferred embodiment, the inert gas flow is typically in the range of 10 to 350 sccm and the flow of the oxygen-containing gas is in the range of 0.02 to 0.15 sccm. Actual flows for the oxygen-containing gas can vary depending on the flow of inert gas, the selection of the oxygen-containing gas, and the type of plasma system used. A typical process 108 used in the Spectra® inductively coupled etch process module manufactured by Tegal Corporation is as follows for a 200 mm diameter silicon substrate: 100 W of 13.56 MHz rf power on the source coil, 20 W of 450 kHz rf power applied to the substrate, 350 sccm Ar, 0.08 sccm $O_2$, and 10 mT process pressure. The conditions provided above for the etch stop, sputter process step 108 are intended to provide an exemplary set of conditions that have been found to produce a sputter selectivity between NiFe and alumina of ~90:1 in the Spectra ICP process module manufactured by Tegal Corporation. (See FIG. 11.)

A range of process conditions and chamber configurations can be used to produce results with high selectivity between the upper magnet material and the dielectric. Two factors that must be considered in achieving high selectivity are the control of the ratio of inert gas to oxygen-containing gas in the process chamber and the operation of the process at low bias power levels. These two factors are discussed in more detail in the following paragraphs.

In the preferred embodiments, the etch stop process requires a high selectivity (>5:1) between the upper magnet layer 20 and the underlying dielectric layer 18. It is expected that the upper magnet layer 20 will be etched at a rate of at least 5 times faster than the rate at which the underlying dielectric layer 18, e.g., $Al_2O_3$, is etched. Precise control of the NiFe/CoFe etch rate is possible because there are significant differences in sputter thresholds between the NiFe and CoFe and that of oxidized metals such as $Al_2O_3$ and MgO. Experiments that confirmed these phenomena were conducted using a Spectra® process module manufactured by Tegal Corporation (Petaluma, Calif.).

Specifically, NiFe and CoFe sputter rates were measured with monolayer test wafers and alumina etch rates were measured with alumina/NiFe test structures. The test structure consisted of a substrate that had a NiFe layer deposited thereon and a very thin layer of alumina (~15 Å) over the NiFe. The measured alumina etch rates were representative of the thin film properties that would be found in stacks containing magnetic tunneling junctions.

Figure 12:
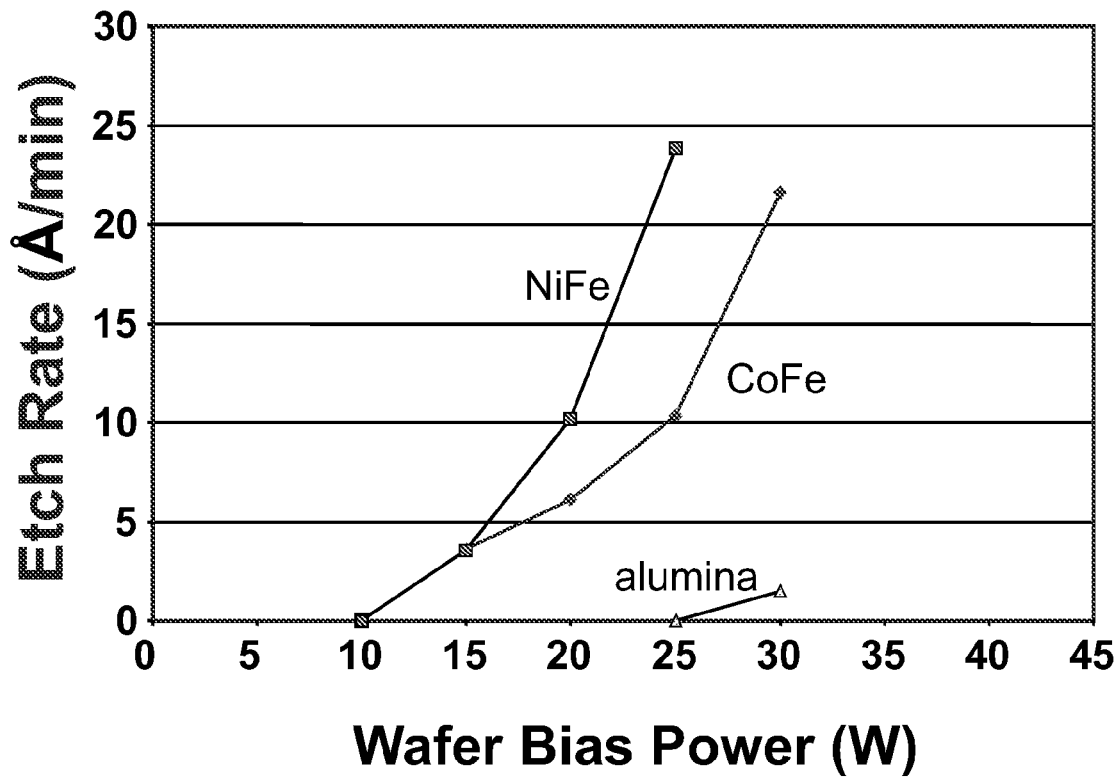
FIG. 12. Graph of etch sputter rates for CoFe, NiFe, and alumina.

As is apparent from the graph in FIG. 12, a significant difference was observed between the onset of sputtering for the magnetic alloys in comparison to that of the alumina. It was further observed in etch rate tests, which were performed on alumina/NiFe test structures at bias power levels greater than 10 W and less than 25 W, that the alumina did not measurably etch. These observations indicate that under specific process conditions, significant amounts of NiFe and CoFe can be etched from a TMR stack while only a small amount of alumina is removed in the same amount of time.

Figure 10:
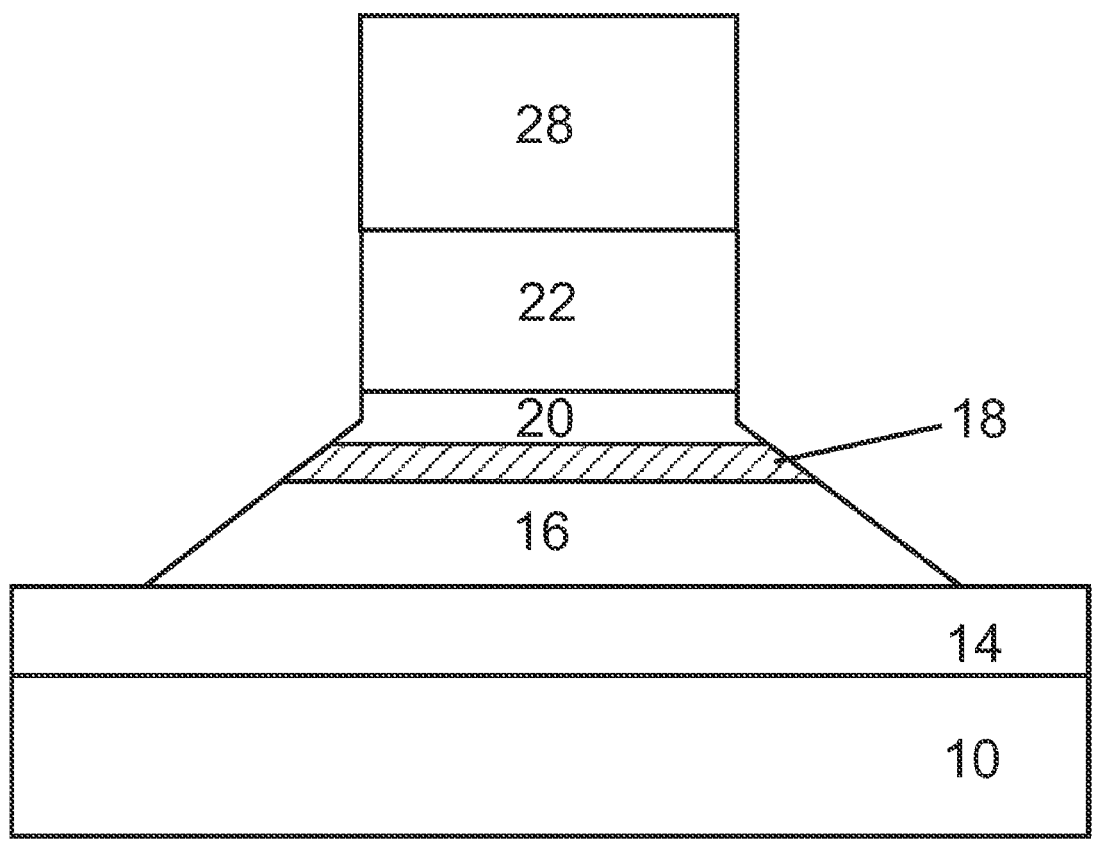
FIG. 10. Embodiment of the inventive MRAM patterning sequence in which the magnetic stack layers are intentionally etched with a sloped profile during a reactive etch step prior to the etch stop process.
Figure 13:
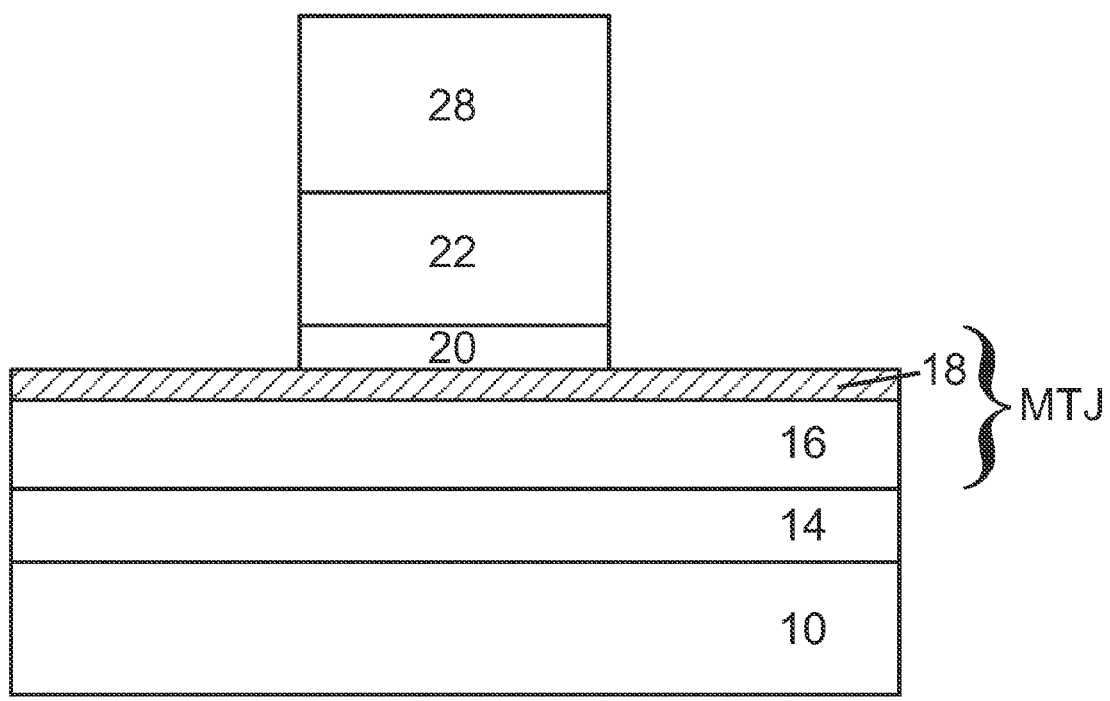
FIG. 13. MRAM stack structure after reactive magnet layer etch (see FIG. 6) and etch stop process.
Figure 14:
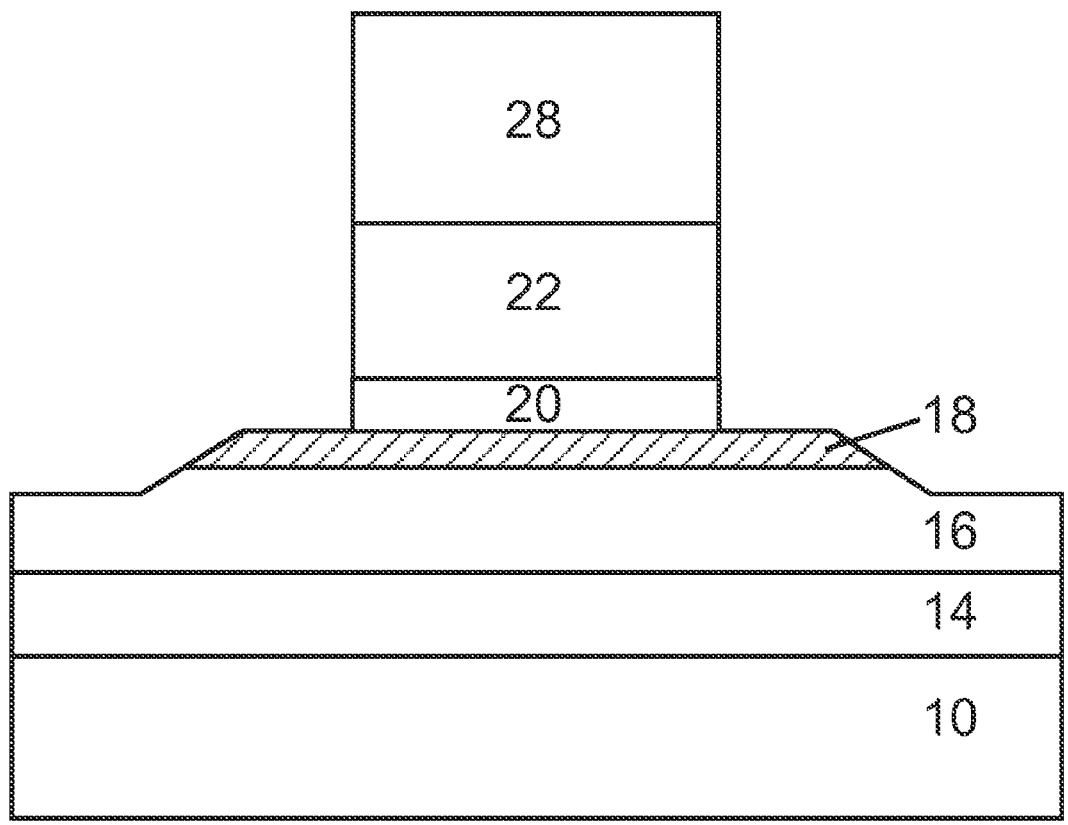
FIG. 14. MRAM stack structure after reactive magnet layer etch (see FIG. 7) and etch stop process.
Figure 15:
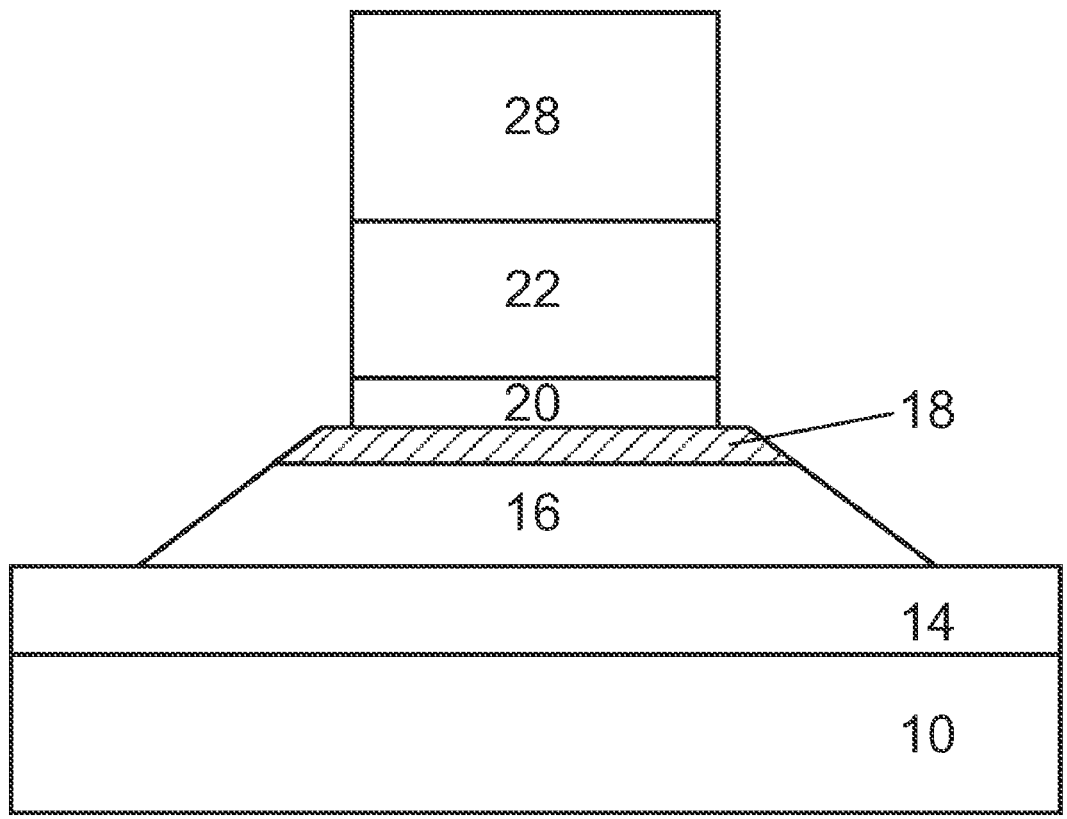
FIG. 15. MRAM stack structure after reactive magnet layer etch (see FIG. 8) and etch stop process.

The resulting device profiles following the preferred embodiments of reactive etch steps 106 as shown in FIGS. 7, 9, and 10 and etch stop process 108 are shown in FIGS. 13, 14, and 15. In each of these embodiments, the residual metal film that remains of upper magnet layer 20 after reactive etch step 106, is removed from the underlying dielectric layer 18. The removal of the upper magnet layer 20 that remains after reactive step 106 with a low bias non-reactive etch stop 108 provides superior electrical isolation over other known methods without damaging the underlying dielectric layer 18. Geometric isolation is provided in each of the three embodiments of the inventive process without the inherent risk of electrical shorting that has been known to limit device performance for structures incorporating MTJ stacks. Superior electrical isolation between the upper magnet layer 20 and the bottom magnet layer 16 is also accomplished with the inventive process without the associated risks involved in using corrosive chemistries at the stage of the process that is most critical for producing reliable devices.

The typical process conditions for etch stop 108 provided above are intended to be representative of a process that was found to yield an exceptionally high selectivity between NiFe or CoFe and alumina. Variations of the process conditions within the Spectra reactor can be used within the scope of the inventive etch stop process 108.

Similar processes utilizing the approach of either one or both of a first step of removing the bulk of the upper magnet layer using a mixture of chlorine and fluorine containing gases and a second step of using a mixture of an inert gas and oxygen-containing gas for stopping on the dielectric tunneling layer can also be developed in other inductively coupled plasma reactors, in capacitively-coupled plasma reactors, electron cyclotron resonance reactors, and in other reactors used to generate plasma for the purpose of manufacturing devices for magnetic films and would still be in the scope of the inventive process. Additionally, use of the mixture of an inert gas and an oxygen-containing gas for the purpose of using the dielectric layer as an etch stop without an initial step of using a mixture of chlorine and fluorine containing gases to remove the bulk of the upper magnet layer is also within the scope of the inventive process.

High selectivity in the exemplary embodiment for etch stop 108 described above between NiFe and alumina is observed using a gas mixture of argon and oxygen. Within the scope of the inventive process, is the use of one or both of alternative inert and oxidizing components of the preferred embodiment of the argon/oxygen gas mixture that was used to demonstrate NiFe/alumina selectivity of ~90:1 in etch stop process 108. Helium, neon, krypton, and nitrogen, for example, can be used in place of, or in combination with argon, to provide the inert component of the etch stop process 108. Similarly, alternatives to oxygen such as $N_2O$, NO, CO, and $CO_2$, among others, can be used in place of, or in combination with oxygen to produce the oxidizing component of the etch stop process 108. Alternatively, within the scope of the inventive process, the oxygen-containing gas can be eliminated by controlling the oxygen level in the etch chamber by a method other than the intentional introduction of an oxygen-containing gas as is discussed in the following paragraphs.

It has been demonstrated when plasma sputtering magnetic layers comprising transition metals such as NiFe with inert sputtering gases such as Ar, that regulating the amount of oxygen in the plasma chamber can influence the etch selectivity with respect to the underlying alumina. That is, a higher NiFe/alumina selectivity can be achieved by controlling the flow of oxygen into the plasma chamber. One embodiment of the plasma overetch process reducing the background oxygen to levels that do not affect the etching process while concurrently re-introducing oxygen in a measurable and controllable manner into the plasma chamber. Sources of the background oxygen that may enter the plasma chamber include, for example: (1) sputtering of oxygen-containing internal chamber parts, (2) atmospheric oxygen; (3) outgassing from materials in the chamber; and (4) other processing modules in the process system.

When "uncontrolled" background oxygen in the chamber is reduced, the selectivity between NiFe and alumina can be optimized by re-introducing a very small amount (e.g., ~0.08 sccm) of oxygen into the chamber. One technique to re-introduce the oxygen employs two separate carrier gas sources that are connected to the chamber. The first source supplies an $Ar/O_2$ gas mixture comprising 99.9% Ar and 0.1% $O_2$ to the plasma chamber while a second source supplies a gas containing 100% Ar in parallel to the chamber. When re-introducing oxygen into the plasma chamber, it is preferred that the base pressure of the chamber be reduced to ~0.001 mT or less. Additionally, the sputtering of the surfaces of internal chamber parts should be minimized or controlled. For example, inductive source power should be low (100-200 W) to minimize window sputtering. Excessive amounts of oxygen in the chamber can slow the etch rate of the metallic magnetic films and can lead to a reduction in selectivity between the magnet layers and the dielectric layers.

Alternatively, in a second technique, oxygen is introduced into the process chamber through an orifice separating a source of oxygen and the process chamber. The orifice is sized such that flow of the oxygen containing gas, when mixed with an inert gas, produces an enhancement in the sputtering selectivity between the upper magnetic film and the tunneling dielectric.

Other means for introducing a controlled level of oxygen into an inert gas to provide the necessary conditions for selectively etching the magnetic material over the dielectric layer can also be used within the scope of this patent. In such embodiments, sputtering of interior surfaces of oxygen-containing materials in the plasma reactor can be used as a source of oxygen. In this embodiment, an inert gas such as argon would be introduced through conventional means, such as a mass flow controller or needle valve, at such a volume so as to produce a mixture of inert gas and oxygen-containing species at the surface of the upper magnetic layer being etched, so as to produce selective removal between the magnetic material and the tunneling dielectric layer. The process conditions would be adjusted such that the magnetic material would be removed at a rate of >5 Å/min and the dielectric layer would be removed at a rate of <1 Å/min.

In another embodiment of this invention, the level of an oxygen-containing gas is provided by controlling the leakage of atmospheric gases into the vacuum chamber. Plasma-based semiconductor fabrication processes are typically performed in the range of 0.1 to 1000 milliTorr. In these sub-atmospheric conditions, oxygen can be introduced inadvertently through imperfect seals, through porous materials, and from outgassing of parts in the processing chamber. The rate of leakage can easily be measured in conventional plasma processing equipment.

In this embodiment, an inert gas such as argon would be introduced through conventional means, such as a mass flow controller or needle valve, at such a volume so as to produce a mixture of inert gas and oxygen-containing species at the surface of the upper magnetic layer being etched, so as to produce selective removal between the magnetic material and the tunneling dielectric layer. Within the scope of this invention is the approach of controlling the oxygen-containing leakage from atmosphere, in combination with the introduction of controlled inert gas flow through conventional means to produce the required mixture of inert gas and oxygen-containing species to the extent that the magnetic material is removed at a rate of >5 Å/min and the dielectric layer is removed at a rate of <1 Å/min.

The process for removing the photoresist and preventing corrosion, namely 112 in FIG. 3, 113 in FIG. 4, 142 in FIG. 5*a*, and 126 and 142 in FIG. 5*b* must be compatible with magnetic film structures. Within the scope of this present invention is the use of hydrogen-containing gas mixtures that are suitable for resist removal and for preventing corrosion that could result from exposure of the MRAM film stack to the halogen-containing etch chemistries. In the preferred embodiments, the magnetic film stack is exposed to a hydrogen-containing plasma to remove photoresist, to expose the magnetic layers to a process that would prevent corrosion upon exposure to ambient conditions, or both. Hydrogen is introduced into the process chamber in a mixture of hydrogen and an inert gas such as helium, neon, argon, or nitrogen.

What is claimed is:

1. A process for fabricating a device wherein the device comprising a top conductive layer over an insulating layer over a bottom conductive layer over a substrate, the process comprising:
   (a) removing a portion of the top conductive layer;
   (b) selectively removing the remaining top conductive layer with respect to the underlying insulating layer; and
   (c) removing a portion of the underlying insulating layer to expose the bottom conductive layer at a location farther than the thickness of the insulating layer.

2. A process as in claim 1 wherein removing a portion of the top conductive layer uses a mixture of fluorine-and chlorine-containing gas.

3. A process as in claim 2 wherein the chlorine-containing gas comprises $Cl_2$, $BCl_3$, HCl, chlorine-containing gas, or any combination thereof.

4. A process as in claim 2 wherein the fluorine-containing gas comprises $CF_4$, $SF_6$, $CHF_3$, fluorine-containing gas, or any combination thereof.

5. A process as in claim 2 wherein a ratio of chlorine-containing gas to fluorine-containing gas is in a range of 2:1 to 20:1.

6. A process as in claim 1 wherein removing a portion of the top conductive layer uses a mixture of $NH_3$ and CO gas.

7. A process as in claim 1 wherein selective removing comprises applying a bias to the substrate with bias power between a sputter threshold of the top conductive layer and the insulating layer to selectively remove the top conductive layer with respect to the underlying insulating layer.

8. A process as in claim 1 wherein the device is a magnetic junction memory device.

9. A process as in claim 1 wherein the insulating layer comprises aluminum oxide, magnesium oxide, or any insulating oxide.

10. A process as in claim 1 wherein the top conductive layer comprises a magnetic layer, part of an MRAM stack structure, or one or more layers of NiFe, CoFe, CoNiFe, and CoFeB.

11. A process for fabricating a device comprising:
   (a) providing a substrate;
   (a1) forming a bottom conductive layer over the substrate;
   (b) forming an insulating layer over the bottom conductive layer;
   (c) forming a top conductive layer over the insulating layer;
   (d) removing a portion of the top conductive layer;
   (e) selectively removing the remaining top conductive layer with respect to the underlying insulating layer; and
   (f) removing a portion of the underlying insulating layer to expose the bottom conductive layer at a location farther than the thickness of the insulating layer.

12. A process as in claim 11 wherein removing a portion of the top conductive layer uses a mixture of fluorine- and chlorine-containing gas.

13. A process as in claim 11 wherein the chlorine-containing gas comprises $Cl_2$, $BCl_3$, HCl, chlorine-containing gas, or any combination thereof.

14. A process as in claim 11 wherein the fluorine-containing gas comprises $CF_4$, $SF_6$, $CHF_3$, fluorine-containing gas, or any combination thereof.

15. A process as in claim 11 wherein a ratio of chlorine-containing gas to fluorine-containing gas is in a range of 2:1 to 20:1.

16. A process as in claim 11 wherein removing a portion of the top conductive layer uses a mixture of $NH_3$ and CO gas.

17. A process as in claim 11 wherein the device is a magnetic junction memory device.

18. A process as in claim 11 further comprising the step of removing the bottom conductive layer under the insulation layer.

19. A process as in claim 11 wherein the insulating layer comprises aluminum oxide, magnesium oxide, or any insulating oxide.

20. A process as in claim 11 wherein the top conductive layer comprises a magnetic layer, part of an MRAM stack structure, or one or more layers of NiFe, CoFe, CoNiFe, and CoFeB.

21. A process for fabricating a device comprising:
   (a) providing a substrate;
   (a1) forming a bottom conductive layer over the substrate;
   (b) forming an insulating layer over the bottom conductive layer;
   (c) forming a top conductive layer over the insulating layer;
   (d) removing a portion of the top conductive layer;
   (e) applying a bias to the substrate with bias power between the sputter threshold of the top conductive layer and the insulating layer to selectively remove the top conductive layer with respect to the underlying insulating layer; and
   (f) removing a portion of the underlying insulating layer to expose the bottom conductive layer at a location farther than the thickness of the insulating layer.

22. A process as in claim 21 wherein removing a portion of the top conductive layer uses a mixture of fluorine-and chlorine-containing gas.

23. A process as in claim 21 wherein the chlorine-containing gas comprises $Cl_2$, $BCl_3$, HCl, chlorine-containing gas, or any combination thereof.

24. A process as in claim 21 wherein the fluorine-containing gas comprises $CF_4$, $SF_6$, $CHF_3$, fluorine-containing gas, or any combination thereof.

25. A process as in claim 21 wherein a ratio of chlorine-containing gas to fluorine-containing gas is in a range of 2:1 to 20:1.

26. A process as in claim 21 wherein removing a portion of the top conductive layer uses a mixture of $NH_3$ and CO gas.

27. A process for fabricating a device comprising:
(a) providing a substrate;
(b) forming an insulating layer over the substrate;
(c) forming a top conductive layer over the insulating layer;
(d) removing a portion of the top conductive layer; and
(e) applying a bias to the substrate with bias power between the sputter threshold of the top conductive layer and the insulating layer to selectively remove the top conductive layer with respect to the underlying insulating layer, and further comprising applying at least one of a non-reactive gas ambient, <1% of an oxygen-containing gas, a mixture of a non-reactive gas and <1% of an oxygen-containing gas, an etch process using a mixture of a non-reactive gas and <1% of an oxygen-containing gas, and a physical sputter process using a mixture of a non-reactive gas and <1% of an oxygen-containing gas.

28. A process as in claim 27 wherein the non-reactive gas is Ar, He, Ne, Kr, N2, or Xe, or any combination thereof, and wherein the oxygen-containing gas is O, $O_2$, $N_2O$, NO, air, CO, or any combination thereof.

29. A process as in claim 27 wherein the mixture is 99.9% Ar and 0.1% $O_2$.

30. A process as in claim 27 wherein the mixture of a non-reactive gas and an oxygen-containing gas is introduced through a first flow controller and a non-reactive gas is introduced through a second flow controller.

31. A process as in claim 30 wherein the first flow controller provides 80 sccm of argon and 0.08 sccm of O2 and the second flow controller provides 270 sccm of argon.

32. A process as in claim 27 wherein the non-reactive gas is in a range of 10 to 350 sccm and the oxygen-containing gas is in the range of 0.02 to 0.15 sccm.

33. A process as in claim 27 wherein the oxygen-containing gas is introduced into the process from the sputtering of a solid source of an oxygen-containing solid.

34. A process as in claim 27 wherein the oxygen-containing gas is introduced from control of leakage from the ambient.

35. A process as in claim 21 wherein the device is a magnetic junction memory device.

36. A process as in claim 21 wherein the insulating layer comprises aluminum oxide, magnesium oxide, or any insulating oxide.

37. A process as in claim 21 wherein the top conductive layer comprises a magnetic layer, part of an MRAM stack structure, or one or more layers of NiFe, CoFe, CoNiFe, and CoFeB.

* * * * *